(12) United States Patent
Lin et al.

(10) Patent No.: US 11,459,291 B2
(45) Date of Patent: Oct. 4, 2022

(54) METHOD OF PREPARATION OF (1R,3S)-3-AMINO-1-CYCLOPENTANOL AND SALT THEREOF

(71) Applicant: Porton Pharma Solutions Ltd., Chongqing (CN)

(72) Inventors: Wenqing Lin, Chongqing (CN); Hongjie Zheng, Chongqing (CN); Jianping Zhu, Chongqing (CN); Yong Zhang, Chongqing (CN); Jianchong Wang, Chongqing (CN)

(73) Assignee: PORTON PHARMA SOLUTIONS LTD., Chongqing (CN)

( * ) Notice: Subject to any disclaimer, the term of this patent is extended or adjusted under 35 U.S.C. 154(b) by 0 days.

(21) Appl. No.: 17/163,532

(22) Filed: Jan. 31, 2021

(65) Prior Publication Data

US 2021/0147339 A1    May 20, 2021

Related U.S. Application Data

(63) Continuation-in-part of application No. PCT/CN2019/097921, filed on Jul. 26, 2019.

(30) Foreign Application Priority Data

Aug. 28, 2018 (CN) .......................... 201810991670.2

(51) Int. Cl.
*C07C 213/08* (2006.01)
*C07C 215/44* (2006.01)

(52) U.S. Cl.
CPC ........ *C07C 213/08* (2013.01); *C07B 2200/07* (2013.01); *C07C 215/44* (2013.01)

(58) Field of Classification Search
None
See application file for complete search history.

(56) References Cited

PUBLICATIONS

Ji et al. (Tetrahedron Letters, 2010, 51, 3789). (Year: 2010).*

\* cited by examiner

*Primary Examiner* — Sudhakar Katakam
*Assistant Examiner* — Jennifer C Sawyer
(74) *Attorney, Agent, or Firm* — Matthias Scholl P.C.; Matthias Scholl

(57) ABSTRACT

Provided is a method of preparation of (1R, 3S)-3-amino-1-cyclopentanol, the method including: contacting N-acyl-hydroxyamine and cyclopentadiene for an asymmetric cycloaddition, to yield a first intermediate I; hydrogenating the first intermediate I to yield a second intermediate II; hydrolyzing, ammonolyzing, hydrazinolyzing, or alcoholyzing an amido bond of the second intermediate II to yield a third intermediate III; and hydrogenating the third intermediate III to yield (1R, 3S)-3-amino-1-cyclopentanol.

4 Claims, No Drawings

METHOD OF PREPARATION OF (1R,3S)-3-AMINO-1-CYCLOPENTANOL AND SALT THEREOF

CROSS-REFERENCE TO RELATED APPLICATIONS

This application is a continuation-in-part of International Patent Application No. PCT/CN2019/097921 with an international filing date of Jul. 26, 2019, designating the United States, now pending, and further claims foreign priority benefits to Chinese Patent Application No. 201810991670.2 filed Aug. 28, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to the field of organic synthesis, and more particularly to a method of preparation of (1R, 3S)-3-amino-1-cyclopentanol and a salt thereof.

Biktarvy is a drug developed by Gilead company for the treatment of HIV. It is composed of Bictegravir (50 mg), Emtricitabine (200 mg) and Tenofovir alfenamide (25 mg). Biktarvy was approved by FDA on Feb. 8, 2018. The structural formula of Bictegravir is as follows:

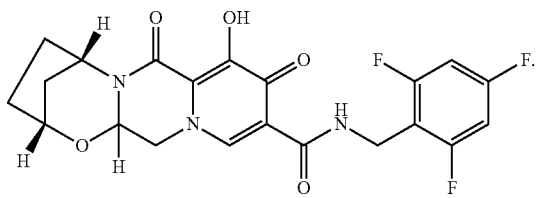 [SMILES: O=C(NCc1c(F)cc(F)cc1F)c1cn2c(c(O)c1=O)C(=O)N1C(C2)O[C@@H]2CC[C@H]1C2]

(1R, 3S)-3-amino-1-cyclopentanol is an intermediate for the synthesis of Bictegravir, and (1R, 3S)-3-amino-1-cyclopentanol contains two chiral centers. Existing synthetic schemes of the intermediate mainly include chiral resolution and chiral synthesis. Chiral resolution includes enzymatic resolution through enzyme and chemical resolution by a chiral acid. The theoretical yield of chiral resolution can only reach 50%, while the actual yield can only reach 30-45%, resulting in the waste of raw materials. Chiral synthesis employs chiral raw materials to synthesize chiral products. However, the chiral raw materials are not easily available, thus leading to high costs.

SUMMARY

One objective of the disclosure is to provide a method for preparing (1R, 3S)-3-amino-1-cyclopentanol and a salt thereof, which has the advantages of easily available raw materials, high utilization rate of raw materials and low production cost. And the method is easy to operate in mild conditions; the resulting product has high optical purity, stable quality, and is suitable for mass production.

The disclosure also provides at least one intermediate for preparation of (1R, 3S)-3-amino-1-cyclopentanol and a salt thereof. The raw materials are easily available and can be used for mass production of the intermediate.

The disclosure provides a method for preparing (1R, 3S)-3-amino-1-cyclopentanol, the method comprising:
contacting N-acylhydroxyamine and cyclopentadiene for an asymmetric cycloaddition, to yield a first intermediate I;
hydrogenating the first intermediate I to yield a second intermediate II;
breaking an amido bond of the second intermediate II to yield a third intermediate III; and
hydrogenating the third intermediate III to yield (1R, 3S)-3-amino-1-cyclopentanol.

The N-acylhydroxyamine has a structural formula of

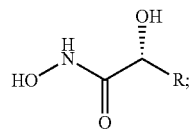

the first intermediate I has a structural formula of

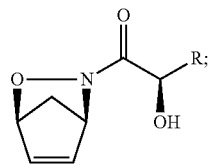

the second intermediate II has a structural formula of

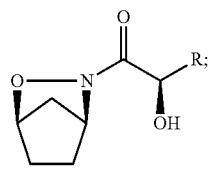

the third intermediate III has a structural formula of

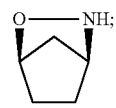

(1R, 3S)-3-amino-1-cyclopentanol has a structural formula of

and R represents a $C_{1-4}$ alkyl or a $C_{6-10}$ aryl.

The disclosure also provides a method of preparation of a salt of (1R, 3S)-3-amino-1-cyclopentanol, the method comprising:
contacting N-acylhydroxyamine and cyclopentadiene for an asymmetric cycloaddition, to yield a first intermediate I;
hydrogenating the first intermediate I to yield a second intermediate II;
alcoholyzing an amido bond of the second intermediate II with an acid as a catalyst to yield a salt of a third intermediate III; and hydrogenating the salt of the third intermediate III to yield a salt of (1R, 3S)-3-amino-1-cyclopentanol.

The N-acylhydroxyamine has a structural formula of

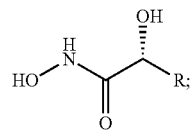

the first intermediate I has a structural formula of

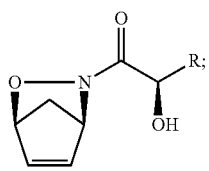

the second intermediate II has a structural formula of

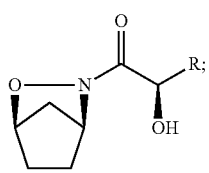

the salt of the third intermediate III has a structural formula of

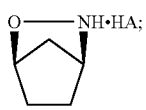

the salt of (1R, 3S)-3-amino-1-cyclopentanol has a structural formula of

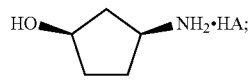

R represents a $C_{1-4}$ alkyl or a $C_{6-10}$ aryl; and HA is HCl, HBr, $H_2SO_4$, p-toluenesulfonic acid (TsOH) or methanesulfonic acid (MsOH).

In one aspect, the disclosure provides a compound for preparation of (1R, 3S)-3-amino-1-cyclopentanol, having a formula of

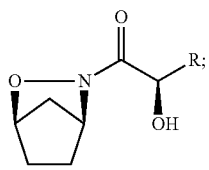

R represents a $C_{1-4}$ alkyl or a $C_{6-10}$ aryl.

In another aspect, the disclosure further provides a compound for preparation of (1R, 3S)-3-amino-1-cyclopentanol, having a formula of

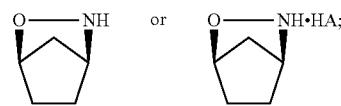

HA is HCl, HBr, $H_2SO_4$, p-toluenesulfonic acid (TsOH) or methanesulfonic acid (MsOH).

Instill another aspect, the disclosure provides use of a compound having a formula of

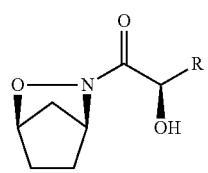

for preparation of (1R, 3S)-3-amino-1-cyclopentanol; R represents a $C_{1-4}$ alkyl or a $C_{6-10}$ aryl.

In still another aspect, the disclosure provides use of a compound having a formula of

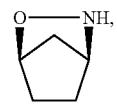

or a salt thereof having a formula of

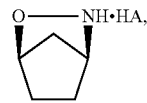

for preparation of (1R, 3S)-3-amino-1-cyclopentanol, where HA is HCl, HBr, $H_2SO_4$, p-toluenesulfonic acid (TsOH) or methanesulfonic acid (MsOH).

In a class of this embodiment, R represents a $C_{2-4}$ alkyl or a $C_{6-10}$ aryl.

In a class of this embodiment, R is selected from the group consisting of methyl, ethyl, n-propyl, isopropyl and tert butyl; for example, R is tert butyl.

In a class of this embodiment, R is tert butyl.

In a class of this embodiment, R is selected from phenyl and substituted phenyl; particularly, R is a phenyl.

The following advantages are associated with the method of preparation of (1R, 3S)-3-amino-1-cyclopentanol of the disclosure. N-acylhydroxyamine comprises a chiral center and is used as a chiral inducer to react with cyclopentadiene for an asymmetric cycloaddition to yield a target product comprising two chiral centers. N-acylhydroxyamine is derived from hydroxyamine which is cheap and easily available. The method is easy to operate, is carried out in mild conditions; the resulting product has high optical purity, stable quality, and is suitable for mass production.

The disclosure also provides at least one intermediate for preparation of (1R, 3S)-3-amino-1-cyclopentanol and a salt thereof. The raw materials are easily available and are suitable for mass production of (1R, 3S)-3-amino-1-cyclopentanol.

DETAILED DESCRIPTION

To further illustrate, embodiments detailing a method of preparation of (1R, 3S)-3-amino-1-cyclopentanol or a salt thereof are described below. It should be noted that the following embodiments are intended to describe and not to limit the disclosure. If the specific conditions are not indicated in the examples, the conventional conditions or the conditions recommended by the manufacturer shall be followed. The reagents or instruments used without manufacturer's indication are conventional products available in the market.

Unless otherwise noted, scientific and technical terms used in the disclosure have the meanings generally understood by those of ordinary skill in the art. Exemplary methods and materials are described below, but those similar or equivalent to those described herein may also be practical in the disclosure.

The following is detailed descriptions of the preparation method of (1R, 3S)-3-amino-1-cyclopentanol in the examples of the disclosure.

The disclosure provides a method of preparation of (1R, 3S)-3-amino-1-cyclopentanol, the method comprising:

contacting N-acylhydroxyamine and cyclopentadiene for an asymmetric cycloaddition, to yield a first intermediate I;

hydrogenating the first intermediate I to yield a second intermediate II;

breaking an amido bond of the second intermediate II to yield a third intermediate III; and hydrogenating the third intermediate III to yield (1R, 3S)-3-amino-1-cyclopentanol.

The N-acylhydroxyamine has a structural formula of

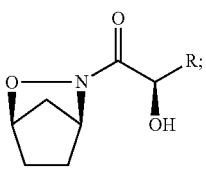

the first intermediate I has a structural formula of

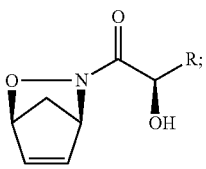

the second intermediate II has a structural formula of

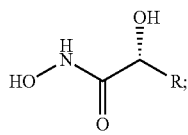

the third intermediate II has a structural formula of

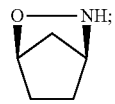

(1R, 3S)-3-amino-1-cyclopentanol has a structural formula of

and R represents a $C_{1-4}$ alkyl or a $C_{6-10}$ aryl.

In certain embodiments, $C_{1-4}$ alkyl in the disclosure is selected from the group consisting of methyl, ethyl, n-propyl, isopropyl and tert butyl. $C_{6-10}$ aryl includes but is not limited to phenyl, naphthyl, and substituted phenyl. Substituted phenyl includes phenyl substituted by alkyl, halogen, nitro and alkoxy on at least one of ortho, meta and para positions. In certain embodiments, R is phenyl.

In certain embodiments, R represents a $C_{2-4}$ alkyl or a $C_{6-10}$ aryl.

In certain embodiments, R is selected from the group consisting of methyl, ethyl, n-propyl, isopropyl and tert butyl; particularly, R is tert butyl.

In certain embodiments, R is tert butyl.

In certain embodiments, the asymmetric cycloaddition between the N-acylhydroxyamine and cyclopentadiene is carried out in the presence of an oxidant selected from periodate, oxygen, hydrogen peroxide and N-bromosuccinimide (NBS), or a mixture thereof, to yield the first intermediate I.

In certain embodiments, the first intermediate I is hydrogenated under hydrogen atmosphere with palladium on carbon (Pd/C) or Raney nickel as a catalyst.

In certain embodiments, when Pd/C is used as the catalyst for hydrogenation of the first intermediate I, the hydrogen pressure is 0.05-0.1 megapascal, and the temperature is between −10 and 15° C.

In certain embodiments, when Raney nickel is used as the catalyst for hydrogenation of the first intermediate I, the hydrogen pressure is 0.1-2 megapascal, and the temperature is between −10 and 15° C.

In certain embodiments, the amido bond of the second intermediate II is hydrolyzed with an acid or base as a catalyst. The acid is selected from the group consisting of hydrochloric acid, hydrogen bromide, sulfuric acid, p-toluenesulfonic acid, methanesulfonic acid, or a mixture thereof. The base is selected from the group consisting of ammonia, hydrazine hydrate, hydroxylamine aqueous solution, sodium methoxide, sodium ethoxide, or a mixture thereof.

In certain embodiments, the amido bond of the second intermediate II is hydrolyzed with the base as a catalyst at a temperature between −10 and 40° C. After the reaction, the reaction liquid is acidified, the aqueous phase is collected, alkalized, and extracted to yield the third intermediate III.

In certain embodiments, the amido bond of the second intermediate II is hydrolyzed with the acid as a catalyst at a temperature between 0 and 60° C. At the reaction, the solution is concentrated to remove the solvent thus yielding a salt of the third intermediate III. It should be noted that in the synthesis process of the salt of the third intermediate III, there is not much difference between acid catalysis and base catalysis in essence. The salt of the third intermediate III can be hydrogenated directly.

In certain embodiments, the third intermediate III or a salt thereof is hydrogenated under hydrogen atmosphere with palladium on carbon (Pd/C) as a catalyst; in the catalytic reaction, the hydrogen pressure is 0.1-1 megapascal, and the temperature is between 20 and 50° C.

In certain embodiments, the disclosure further provides a method of preparation of a salt of (1R, 3S)-3-amino-1-cyclopentanol, the method comprising:

contacting N-acylhydroxyamine and cyclopentadiene for an asymmetric cycloaddition, to yield a first intermediate I;

hydrogenating the first intermediate I to yield a second intermediate II;

alcoholyzing an amido bond of the second intermediate II with an acid as a catalyst to yield a salt of a third intermediate III; and hydrogenating the salt of the third intermediate III to yield a salt of (1R, 3S)-3-amino-1-cyclopentanol.

The N-acylhydroxyamine has a structural formula of

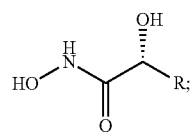

the first intermediate I has a structural formula of

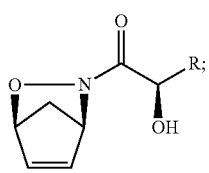

the second intermediate II has a structural formula of

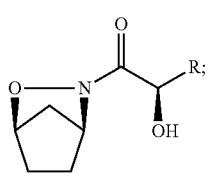

the salt of the third intermediate III has a structural formula of

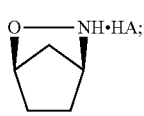

the salt of (1R, 3S)-3-amino-1-cyclopentanol has a structural formula of

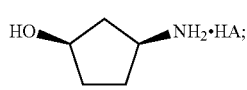

R represents a $C_{1-4}$ alkyl or a $C_{6-10}$ aryl; and HA is HCl, HBr, $H_2SO_4$, p-toluenesulfonic acid (TsOH) or methanesulfonic acid (MsOH).

In certain embodiments, the amido bond of the second intermediate II is alcoholyzed at a temperature between 0 and 60° C. The acid is HCl, HBr, $H_2SO_4$, p-toluenesulfonic acid (TsOH) or methanesulfonic acid (MsOH), or a mixture thereof.

In certain embodiments, the salt of the third intermediate III is hydrogenated under hydrogen atmosphere with palladium on carbon (Pd/C) or Raney nickel as a catalyst.

In certain embodiments, when Pd/C is used as the catalyst for hydrogenation of the third intermediate III, the hydrogen pressure is 0.1-1 megapascal, and the temperature is between 20 and 50° C.

In certain embodiments, when Raney nickel is used as the catalyst for hydrogenation of the third intermediate III, the hydrogen pressure is 0.1-2 megapascal, and the temperature is between 20 and 50° C.

The disclosure also provides a compound for preparation of (1R, 3S)-3-amino-1-cyclopentanol, having a formula of

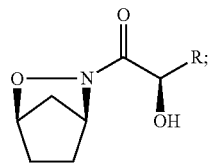

R represents a $C_{1-4}$ alkyl or a $C_{6-10}$ aryl.

In certain embodiments, R is selected from phenyl and substituted phenyl, for example, R is phenyl.

In certain embodiments, R represents a $C_{2-4}$ alkyl or a $C_{6-10}$ aryl.

In certain embodiments, R is selected from the group consisting of methyl, ethyl, n-propyl, isopropyl and tert butyl, particularly, from the group consisting of ethyl, n-propyl, isopropyl and tert butyl, and more particularly, R is tert butyl.

In certain embodiments, R is selected from the group consisting of methyl, ethyl, n-propyl, isopropyl and tert butyl.

In certain embodiments, R is tert butyl.

The disclosure also provides a compound for preparation of (1R, 3S)-3-amino-1-cyclopentanol, having a formula of

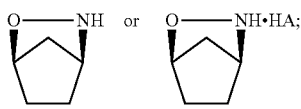

HA is HCl, HBr, $H_2SO_4$, p-toluenesulfonic acid (TsOH) or methanesulfonic acid (MsOH).

In certain embodiments, HA is HCl.

The features and performance of the compound of the disclosure are further described in detail in combination with examples.

Example 1

A preparation method of the first intermediate I is provided. The reaction formula is as follows:

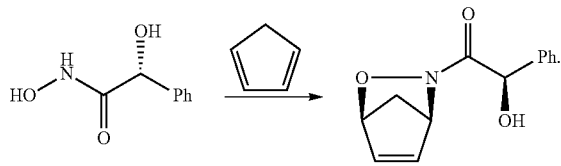 [SMILES: O=C(NO)[C@H](O)c1ccccc1 ; C1=CCC=C1 ; O=C([C@H](O)c1ccccc1)N1O[C@@H]2C=C[C@H]1C2]

Specifically, 83.5 g of N-acylhydroxyamine ((R)—N,2-dihydroxy-2-phenylacetamide) and 300 mL of methanol were added to a reactor. The mixture was stirred until N-acylhydroxyamine was completely dissolved. The mixture was cooled to −10° C., and cyclopentadiene and sodium periodate aqueous solution were added. Thereafter, the solution was filtered and the filtrate was collected. Saturated sodium bisulfite was added to the filtrate for quenching reaction. Methanol was removed by vacuum concentration. Ethyl acetate was added to the water phase twice for extraction reaction. The extract liquids were combined, dried over anhydrous sodium sulfate, filtered, and concentrated to yield the first intermediate I (99.7 g, yield: 86.3%, dr=3.5/1, de>95% after recrystallization).

Example 2

A preparation method of the first intermediate I is provided. The reaction formula is as follows:

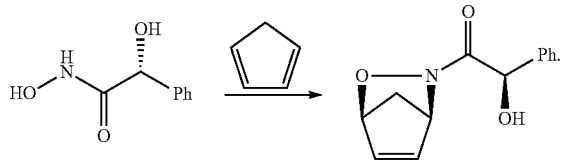 [SMILES: O=C(NO)[C@H](O)c1ccccc1 ; C1=CCC=C1 ; O=C([C@H](O)c1ccccc1)N1O[C@@H]2C=C[C@H]1C2]

Specifically, 25 g of N-acylhydroxyamine ((R)—N, 2-dihydroxy-2-phenylacetamide), 200 mL of tetrahydrofuran, 1 mol % cuprous chloride as a catalyst (that is, catalyst:(R)—N,2-dihydroxy-2-phenylacetamide=1 mol:100 mol), pyridine, and newly evaporated cyclopentadiene were added to a reactor. The mixture was stirred evenly. Oxygen was constantly introduced to the reactor until the reaction was completed. 5% ethylene diamine tetraacetic acid (EDTA) solution was added to the reaction solution, stirred, rested, and filtered. The filtrate was concentrated and tetrahydrofuran was removed. The water phase was extracted thrice with ethyl acetate. The extract liquids were combined, dried over anhydrous sodium sulfate, filtered, and concentrated to yield the first intermediate I (22.4 g, yield: 64.8%, dr=1.5/1).

Example 3

A preparation method of the first intermediate I is provided. The reaction formula is as follows:

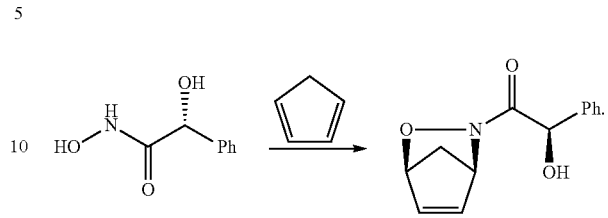

Specifically, 50 g of N-acylhydroxyamine ((R)—N, 2-dihydroxy-2-phenylacetamide), 250 mL of tetrahydrofuran, 0.05 g of Ir(COD)Cl as a catalyst, and cyclopentadiene were added to a reactor. The mixture was cooled to 0° C., and 30% hydrogen peroxide aqueous solution was added. Thereafter, methyl tert-butyl ether was added to the mixture for extraction. The organic phase was dried over anhydrous sodium sulfate, filtered, and concentrated to yield the first intermediate I (63 g, yield: 91.1%, dr=3/1).

Example 4

A preparation method of the first intermediate I is provided. The reaction formula is as follows:

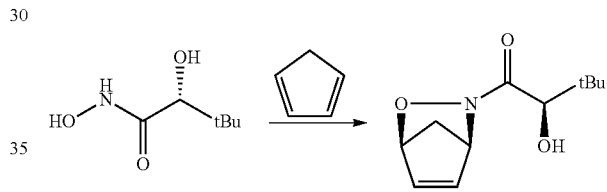

Specifically, 100 g of N-acylhydroxyamine ((R)—N, 2-dihydroxy-2-tert-butyl acetamide), 300 mL of dichloromethane, pyridine, and cyclopentadiene were added to a reactor. The mixture was cooled to −20° C., and N-bromosuccinimide (NBS) was added. Thereafter, water was added to the mixture for quenching reaction. The mixture was rested for layering. The water phase was extracted with dichloromethane, and the organic phases were combined. The organic phase was dried over anhydrous sodium sulfate, filtered, and concentrated to yield the first intermediate I (85 g, yield: 59.2%, dr=4.5/1).

Example 5

A preparation method of the second intermediate II is provided. The reaction formula is as follows:

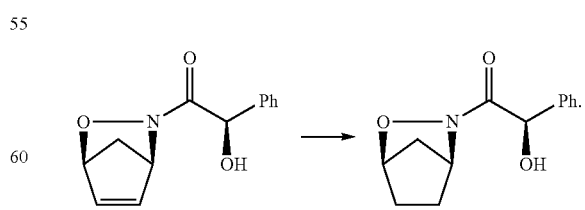

Specifically, 12.0 g of the first intermediate I, 100 mL of methanol, and 0.6 g 10% Pd/C were added to a hydrogenation reactor. The reactor cover was closed. Nitrogen was introduced to the reactor to replace air, and then hydrogen was introduced to the reactor to replace nitrogen. The hydrogen pressure was 0.1 megapascal and the temperature was −5° C. Thereafter, the reactor cover was removed. The reaction solution was collected, filtered, concentrated, and recrystallized to yield the second intermediate II (white solid, 7.6 g, yield: 62.8%).

The second intermediate II was characterized as follows:

$^1$H-NMR (CDCl$_3$, 400 MHz): δ ppm 7.21-7.41 (m, 5H), 5.23 (d, 1H, J=6.4 Hz), 4.84 (s, 1H), 4.66 (s, 1H), 4.25 (d, 1H, J=6.8 Hz), 1.95-2.10 (m, 1H), 1.69-1.75 (m, 1H), 1.53-1.65 (m, 2H), 1.39-1.52 (m, 1H), 0.92-1.05 (m, 1H).

$^{13}$C-NMR (CDCl$_3$, 100 MHz): δ ppm 169.52, 145.53, 139.01, 128.23, 128.04, 127.42, 80.54, 71.12, 57.38, 38.31, 28.07, 27.84.

HRMS: the detection value was 234.1169; the theoretical value was 234.1125 (calculated by $C_{13}H_{16}NO_3^+$).

Example 6

A preparation method of the second intermediate II is provided. The reaction formula is as follows:

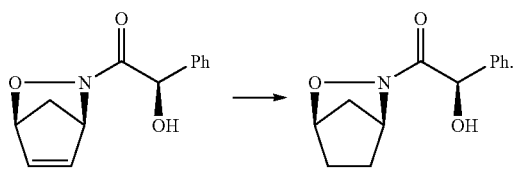 [SMILES: O=C([C@H](O)c1ccccc1)N1O[C@@H]2C=C[C@H]1C2 ; O=C([C@H](O)c1ccccc1)N1O[C@@H]2CC[C@H]1C2]

Specifically, 41.2 g of the first intermediate I, 100 mL of methanol, and 11 g of Raney nickel were added to a hydrogenation reactor. The reactor cover was closed. Nitrogen was introduced to the reactor to replace air, and then hydrogen was introduced to the reactor to replace nitrogen. The hydrogen pressure was 0.1 megapascal and the temperature was 15° C. Thereafter, the reactor cover was removed. The reaction solution was collected, filtered, concentrated, and recrystallized to yield the second intermediate II (white solid, 38.5 g, yield (ratio of actual weight to theoretical weight): 92.6%).

Example 7

A preparation method of the second intermediate II is provided. The reaction formula is as follows:

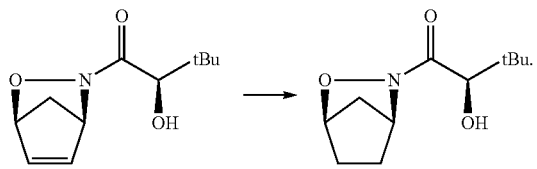 [SMILES: CC(C)(C)[C@@H](O)C(=O)N1O[C@@H]2C=C[C@H]1C2 ; CC(C)(C)[C@@H](O)C(=O)N1O[C@@H]2CC[C@H]1C2]

Specifically, 12.0 g of the first intermediate I, 50 mL of tetrahydrofuran, and 2.2 g of Raney nickel were added to a hydrogenation reactor. The reactor cover was closed. Nitrogen was introduced to the reactor to replace air, and then hydrogen was introduced to the reactor to replace nitrogen. The hydrogen pressure was 2.0 megapascal and the temperature was −5° C. Thereafter, the reactor cover was removed. The reaction solution was collected, filtered, concentrated, and recrystallized to yield the second intermediate II (white solid, 9.73 g, yield: 80.3%).

Example 8

A preparation method of the third intermediate III is provided. The reaction formula is as follows:

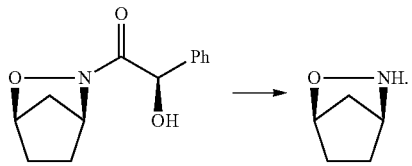 [SMILES: O=C([C@H](O)c1ccccc1)N1O[C@@H]2CC[C@H]1C2 ; C1C[C@@H]2C[C@H]1NO2]

Specifically, 5 g of the second intermediate II and 25 mL of 25 wt. % ammonia/methanol solution were added to a stainless-steel pressure reactor. The reactor cover was closed and the mixture was heated to 40° C. Thereafter, the reaction solution was collected and concentrated under vacuum. Methyl tert-butyl ether and 2 M hydrochloric acid solution were added to the concentrated residue for layering. The water layer was alkalified using 2 M sodium hydroxide, extracted with methyl tert-butyl ether. The extract liquids were combined, dried over anhydrous sodium sulfate, filtered, and concentrated to yield the third intermediate III (1.2 g, yield: 56.7%).

Example 9

A preparation method of the third intermediate III is provided. The reaction formula is as follows:

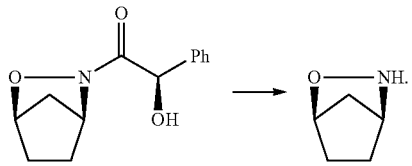 [SMILES: O=C([C@H](O)c1ccccc1)N1O[C@@H]2CC[C@H]1C2 ; C1C[C@@H]2C[C@H]1NO2]

Specifically, 10 g of the second intermediate II, 30 mL of methanol, and 80 wt. % hydrazine hydrate solution were added to a reactor at 25° C. Thereafter, 2 M hydrochloric acid solution was added to the reactor for acidification. The mixture was extracted with dichloromethane. The water phase was alkalified with 2 M sodium hydroxide, and extracted with dichloromethane. The extract liquids were combined, dried over anhydrous sodium sulfate, filtered, and concentrated to yield the third intermediate III (2.6 g, yield: 61.3%).

Example 10

A preparation method of the third intermediate III is provided. The reaction formula is as follows:

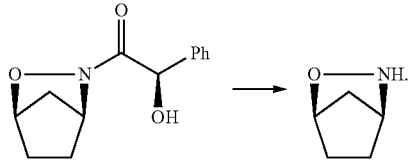

Specifically, 10 g of the second intermediate II, 30 mL of methanol, and 50 wt. % hydroxylamine aqueous solution were added to a reactor. The mixture was heated to 50° C. Thereafter, 2 M hydrochloric acid solution was added to the reactor for acidification. Methanol was evaporated. The water phase was extracted by dichloromethane, alkalified with 2 M sodium hydroxide, and extracted with dichloromethane. The extract liquids were combined, dried over anhydrous sodium sulfate, filtered, and concentrated to yield the third intermediate III (3.2 g, yield: 75.4%).

Example 11

A preparation method of the third intermediate III is provided. The reaction formula is as follows:

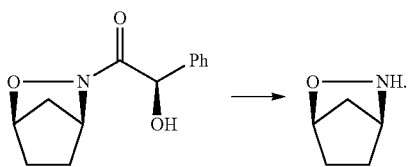 [SMILES: O=C([C@H](O)c1ccccc1)N1O[C@@H]2CC[C@H]1C2 ; C1C[C@@H]2C[C@H]1NO2]

Specifically, 17.50 g of the second intermediate II and 20% of sodium methoxide in methanol were added to a reactor. The mixture was cooled to −10° C. Thereafter, 2 M hydrochloric acid solution was added to the reactor for acidification. Methanol was evaporated. The water phase was extracted by dichloromethane, alkalified with 2 M sodium hydroxide, and extracted with dichloromethane. The extract liquids were combined, dried over anhydrous sodium sulfate, filtered, and concentrated to yield the third intermediate III (6.1 g, yield: 82.1%).

Example 12

A preparation method of the third intermediate III is provided. The reaction formula is as follows:

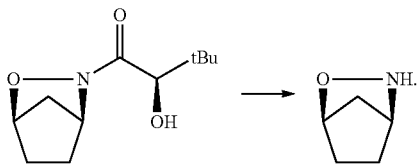 [SMILES: CC(C)(C)[C@@H](O)C(=O)N1O[C@@H]2CC[C@H]1C2 ; C1C[C@@H]2C[C@H]1NO2]

Specifically, 17.50 g of the second intermediate II and 20 mL of absolute ethyl alcohol were added to a reactor. The mixture was cooled to 10° C. Sodium ethoxide was added to the reactor and the temperature was held at 10° C. Thereafter, 2 M hydrochloric acid solution was added to the reactor for acidification. Ethyl alcohol was evaporated. The water phase was extracted by dichloromethane, alkalified with 2 M sodium hydroxide, and extracted with dichloromethane. The extract liquids were combined, dried over anhydrous sodium sulfate, filtered, and concentrated to yield the third intermediate III (6.0 g, yield: 80.7%).

Example 13

A preparation method of a hydrochloride of the third intermediate III is provided. The reaction formula is as follows:

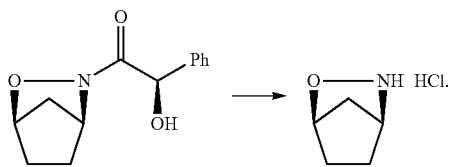 [SMILES: O=C([C@H](O)c1ccccc1)N1O[C@@H]2CC[C@H]1C2 ; C1C[C@@H]2C[C@H]1NO2]

Specifically, 5 g of the second intermediate II and 30 mL of 4 M hydrogen chloride/methanol solution were added to a reactor. The mixture was held at 0° C. until the raw materials disappeared. The mixture was concentrated, and a white solid was obtained. The solid was washed with acetone, filtered and dried to obtain a hydrochloride of the third intermediate III (1.9 g, yield: 65.2%).

The third intermediate III was characterized as follows:

$^{1}$H-NMR (D$_2$O, 400 MHz): δ ppm 5.02-5.04 (m, 1H), 4.51-4.54 (m, 1H), 2.14-2.21 (m, 2H), 1.92-1.99 (m, 2H), 1.87-1.92 (m, 2H).

$^{13}$C-NMR (D$_2$O, 100 MHz): δ ppm 82.37, 60.04, 37.70, 28.09, 23.86.

HRMS: the detection value was 100.0814; the theoretical value was 100.0757 (calculated by C$_5$H$_{10}$NO$^+$).

Example 14

A preparation method of a hydrobromate of the third intermediate III is provided. The reaction formula is as follows:

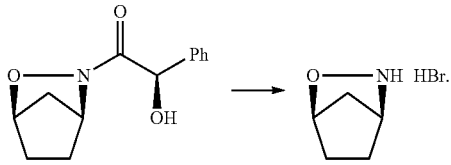

Specifically, 5 g of the second intermediate II and 30 mL of 2 M hydrogen bromide/ethanol solution were added to a reactor. The mixture was held at 10° C. until the raw materials disappeared. The mixture was concentrated, and a white solid was obtained. The solid was washed with methyl tertiary butyl ether, filtered and dried to obtain a hydrobromate of the third intermediate III (2.1 g, yield: 54.4%).

Example 15

A preparation method of a sulfate of the third intermediate III is provided. The reaction formula is as follows:

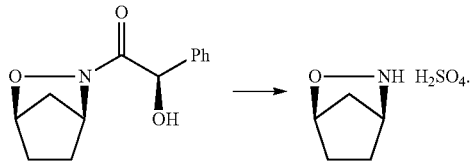

Specifically, 8.5 g of the second intermediate II, 3 mL of concentrated sulfuric acid and 30 mL of methanol solution were added to a reactor. The mixture was held at 25° C. until the raw materials disappeared. The mixture was concentrated, and a white solid was obtained. The solid was washed with ethyl acetate, filtered and dried to obtain a sulfate of the third intermediate III (3.3 g, yield: 46.6%).

Example 16

A preparation method of a tosilate of the third intermediate III is provided. The reaction formula is as follows:

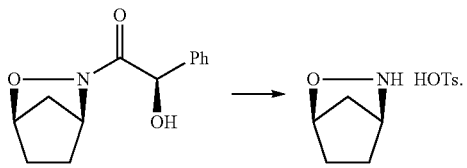

Specifically, 3.5 g of the second intermediate II, 2.85 g of p-toluenesulfonic acid, and 35 mL of methanol were added to a reactor. The mixture was heated to 60° C. until the raw materials disappeared. The mixture was concentrated under vacuum. The residue was washed with acetone, filtered and dried to obtain a tosilate of the third intermediate III (2.2 g, yield: 54.0%).

Example 17

A preparation method of a mesylate of the third intermediate III is provided. The reaction formula is as follows:

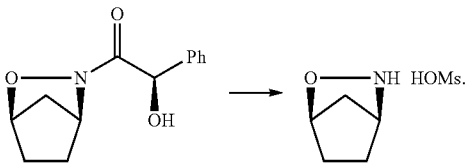

Specifically, 3 g of the second intermediate II, 1.6 g of methanesulfonic acid, and 30 mL of methanol were added to a reactor. The mixture was heated to 40° C. until the raw materials disappeared. The mixture was concentrated under vacuum, to obtain a mesylate of the third intermediate III (oily liquid).

Example 18

A preparation method of (1R, 3S)-3-amino-1-cyclopentanol is provided. The reaction formula is as follows:

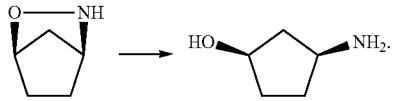 [SMILES: C1C[C@@H]2C[C@H]1NO2 ; N[C@H]1CC[C@@H](O)C1]

Specifically, 3.2 g of the third intermediate III, 20 mL of methanol, and 0.3 g of 10% palladium on carbon (Pd/C) was added to a reactor. Hydrogen was introduced to the reactor and the pressure therein was 0.1 megapascal. The temperature was 30° C. for 24 hours. The mixture was filtered and concentrated to yield a crude product. The crude product was filtered and dried to yield (1R, 3S)-3-amino-1-cyclopentanol (white solid, 2.6 g, yield: 81.0%, optical purity>99.5%).

(1R, 3S)-3-amino-1-cyclopentanol was characterized as follows:

$^1$H-NMR (D$_2$O, 400 MHz): δ ppm 4.28-4.32 (m, 1H), 3.61-3.67 (m, 1H), 2.13-2.21 (m, 1H), 2.02-2.11 (m, 1H), 1.70-1.86 (m, 3H), 1.60-1.66 (m, 1H).

Example 19

A preparation method of a hydrochloride of (1R, 3S)-3-amino-1-cyclopentanol is provided. The reaction formula is as follows:

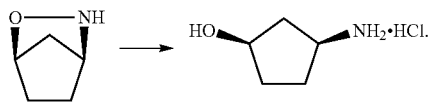

Specifically, 12 g of the third intermediate III, 60 mL of methyl tertiary butyl ether, and 1.0 g of 10% palladium on carbon (Pd/C) was added to a reactor. Hydrogen was introduced to the reactor and the pressure therein was 1.0 megapascal. The temperature was 20° C. for 24 hours. The mixture was filtered and Pd/C was removed. Dry HCl gas was introduced to the filtrate to yield a crude product. The crude product was filtered and dried to yield a hydrochloride of (1R, 3S)-3-amino-1-cyclopentanol (white solid, 9.7 g, yield: 58.2%, optical purity>99.5%).

Example 20

A preparation method of a hydrochloride of (1R, 3S)-3-amino-1-cyclopentanol is provided. The reaction formula is as follows:

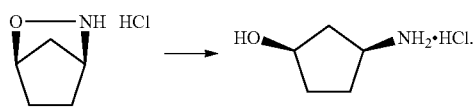

Specifically, 12.7 g of a hydrochloride of the third intermediate III was dissolved in 200 mL of isopropanol. The solution was transferred to a stainless-steel pressure reactor. 2.3 g of palladium on carbon (Pd/C) was added to the reactor. Hydrogen was introduced to the reactor and the pressure therein was 1.0 megapascal. The temperature was 50° C. Thereafter, the mixture was filtered and Pd/C was removed. The filtrate was concentrated, dispersed in 60 mL of anhydrous acetonitrile, filtered, and dried, to yield a hydrochloride of (1R, 3S)-3-amino-1-cyclopentanol (white solid, 5.76 g, yield: 45.3%, optical purity>99.5%).

In conclusion, the disclosure provides a method of preparation of (1R, 3S)-3-amino-1-cyclopentanol and a salt thereof. N-acylhydroxyamine comprising a chiral center is used as a chiral inducer to react with cyclopentadiene for an asymmetric cycloaddition to yield a target product comprising two chiral centers. N-acylhydroxyamine is derived from hydroxyamine which is cheap and easily available. The method is easy to operate, is carried out in mild conditions; the resulting product has high optical purity, stable quality, and is suitable for mass production.

The disclosure also provides at least one intermediate for preparation of (1R, 3S)-3-amino-1-cyclopentanol and a salt thereof. The raw materials are easily available and are suitable for mass production of (1R, 3S)-3-amino-1-cyclopentanol and a salt thereof.

It will be obvious to those skilled in the art that changes and modifications may be made, and therefore, the aim in the appended claims is to cover all such changes and modifications.

INDUSTRIAL APPLICABILITY

The disclosure provides a method of preparation of (1R, 3S)-3-amino-1-cyclopentanol and a salt thereof. N-acylhydroxyamine comprising a chiral center is used as a chiral inducer to react with cyclopentadiene for an asymmetric cycloaddition to yield a target product comprising two chiral centers. N-acylhydroxyamine is derived from hydroxyamine which is cheap and easily available. The method is easy to operate, is carried out in mild conditions; the resulting product has high optical purity, stable quality, and is suitable for mass production.

The disclosure also provides at least one intermediate for preparation of (1R, 3S)-3-amino-1-cyclopentanol and a salt thereof. The raw materials are easily available and are suitable for mass production of (1R, 3S)-3-amino-1-cyclopentanol and a salt thereof.

It will be obvious to those skilled in the art that changes and modifications may be made, and therefore, the aim in the appended claims is to cover all such changes and modifications.

What is claimed is:

1. A compound for preparation of (1R, 3S)-3-amino-1-cyclopentanol, having a formula of

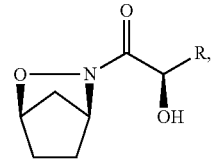

wherein R represents a $C_{1-4}$ alkyl or a $C_{6-10}$ aryl.

2. The compound of claim 1, wherein R represents a $C_{2-4}$ alkyl.

3. The compound of claim 1, wherein R is selected from the group consisting of methyl, ethyl, n-propyl, isopropyl and tert butyl.

4. The compound of claim 1, wherein R is selected from phenyl and substituted phenyl.

* * * * *